US010500326B2

United States Patent
Gillespie et al.

(10) Patent No.: US 10,500,326 B2
(45) Date of Patent: Dec. 10, 2019

(54) BAG OPENING SYSTEM

(71) Applicant: ISOPURE, CORP., Louisville, KY (US)

(72) Inventors: Kevin C. Gillespie, Simpsonville, KY (US); Zachary Patrick Ford, Louisville, KY (US); Guillermo J. Cohen Freue, Bryn Mawr, PA (US)

(73) Assignee: ISOPURE, CORP., Louisville, KY (US)

( * ) Notice: Subject to any disclaimer, the term of this patent is extended or adjusted under 35 U.S.C. 154(b) by 0 days.

(21) Appl. No.: 16/013,690

(22) Filed: Jun. 20, 2018

(65) Prior Publication Data
US 2018/0361047 A1 Dec. 20, 2018

Related U.S. Application Data

(60) Provisional application No. 62/522,484, filed on Jun. 20, 2017.

(51) Int. Cl.
*B65B 69/00* (2006.01)
*A61M 1/16* (2006.01)
*B01F 15/02* (2006.01)

(52) U.S. Cl.
CPC .......... *A61M 1/1666* (2014.02); *A61M 1/167* (2014.02); *B01F 15/0206* (2013.01); *B65B 69/00* (2013.01); *B65B 69/0008* (2013.01); *B65B 69/0033* (2013.01); *B65B 69/0091* (2013.01); *B01F 2215/0034* (2013.01)

(58) Field of Classification Search
CPC .......... B65B 69/033; B65B 69/0008; B01F 15/0206
See application file for complete search history.

(56) References Cited

U.S. PATENT DOCUMENTS

| 3,482,718 A | 12/1969 | Moriarty | |
|---|---|---|---|
| 3,680,725 A | 8/1972 | Poulton | |
| 5,613,824 A * | 3/1997 | Kato | B65B 69/0008 141/114 |
| 5,813,192 A * | 9/1998 | White | B65B 69/0008 141/114 |
| 2009/0304463 A1* | 12/2009 | Dance | B65B 69/0008 406/122 |

FOREIGN PATENT DOCUMENTS

| JP | S5019594 A | 3/1975 |
|---|---|---|
| WO | 2004052727 A1 | 6/2004 |

OTHER PUBLICATIONS

European Patent Office, International Search Report and Written Opinion for PCT/US2018/038581 dated Sep. 4, 2018, 10 pages.

* cited by examiner

*Primary Examiner* — Mark C Hageman
(74) *Attorney, Agent, or Firm* — Middleton Reutlinger

(57) ABSTRACT

A system and apparatus for opening and emptying a bag of material includes a base having a pair of opposed sides and a central aperture through which material may flow. The system includes a pair of opposed doors rotatably mounted on a pair of door shafts, the edges of the pair of opposed doors forming an opening and a plurality of piercing blades pivotally mounted to the base on a pivot rod, the blades capable of pivoting to pierce said bag. The system further includes a cutting blade mounted transversely below the opening of the opposed doors, the cutting blade capable of linear motion across the opening.

17 Claims, 15 Drawing Sheets

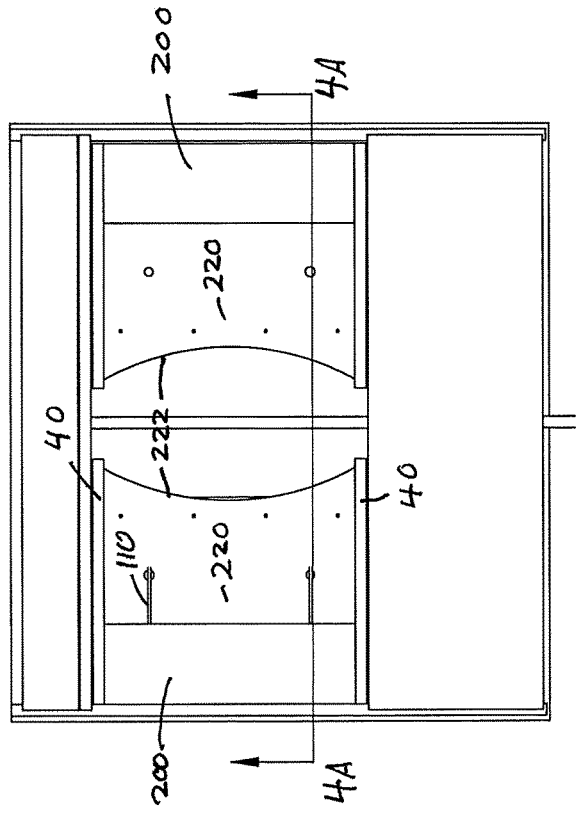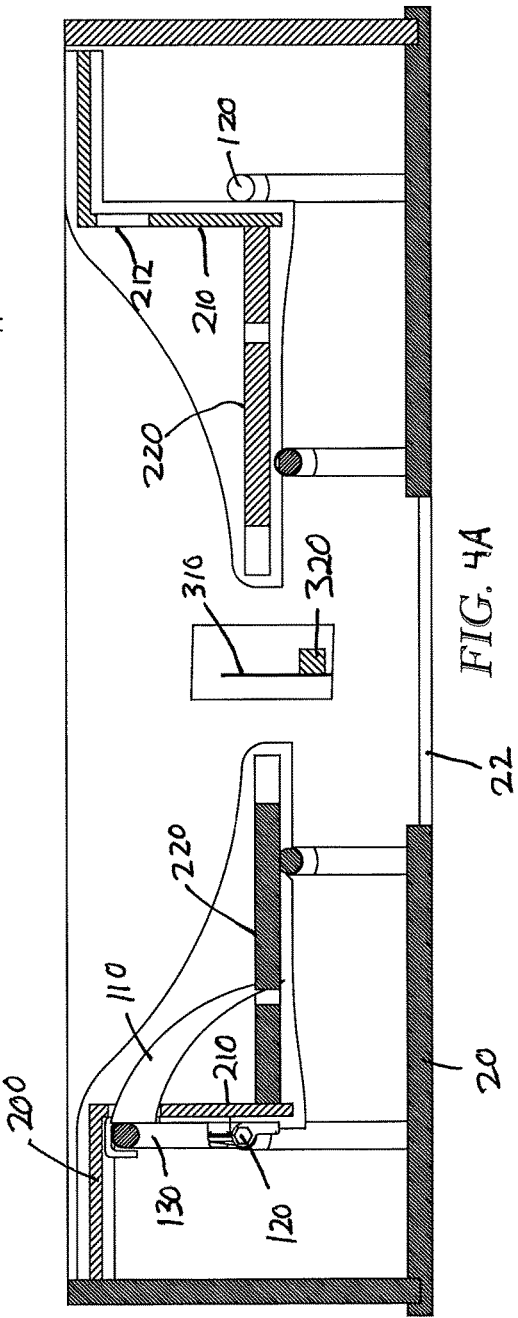
FIG. 4
FIG. 4A

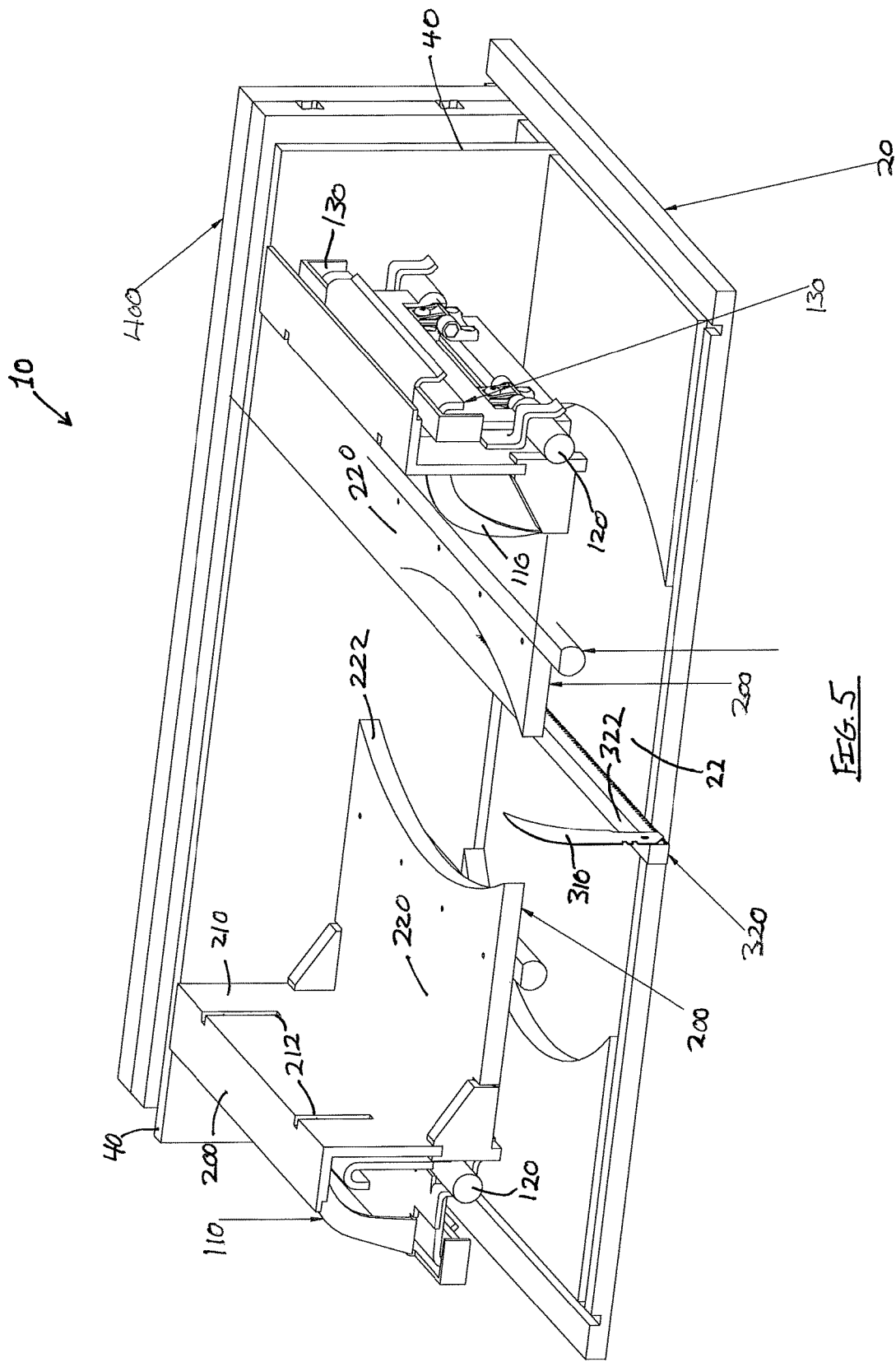

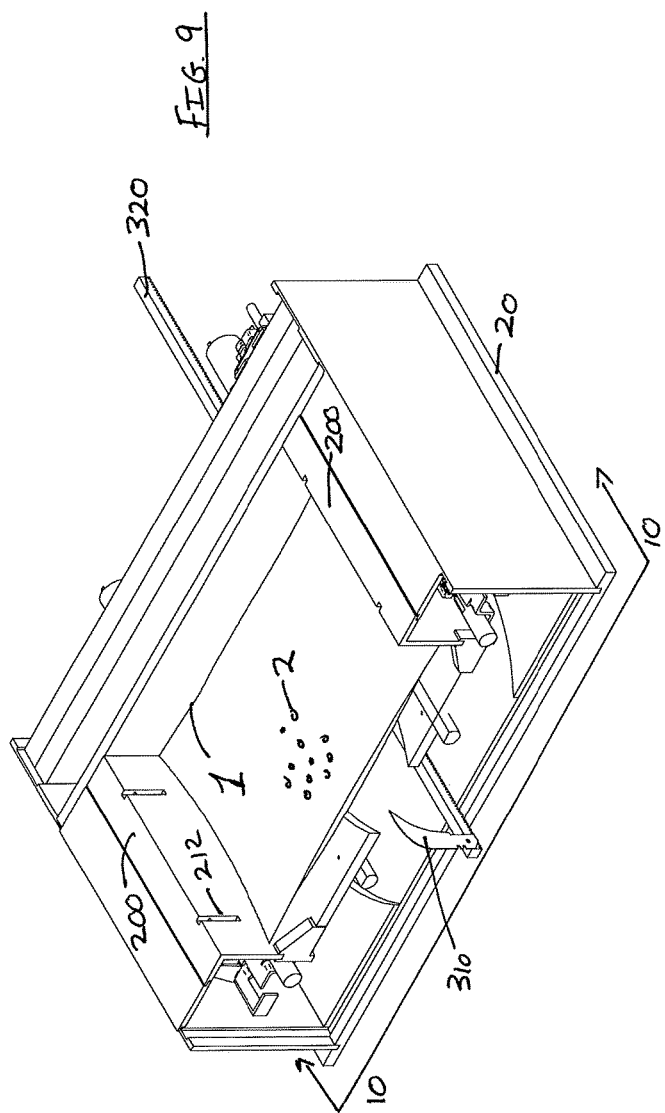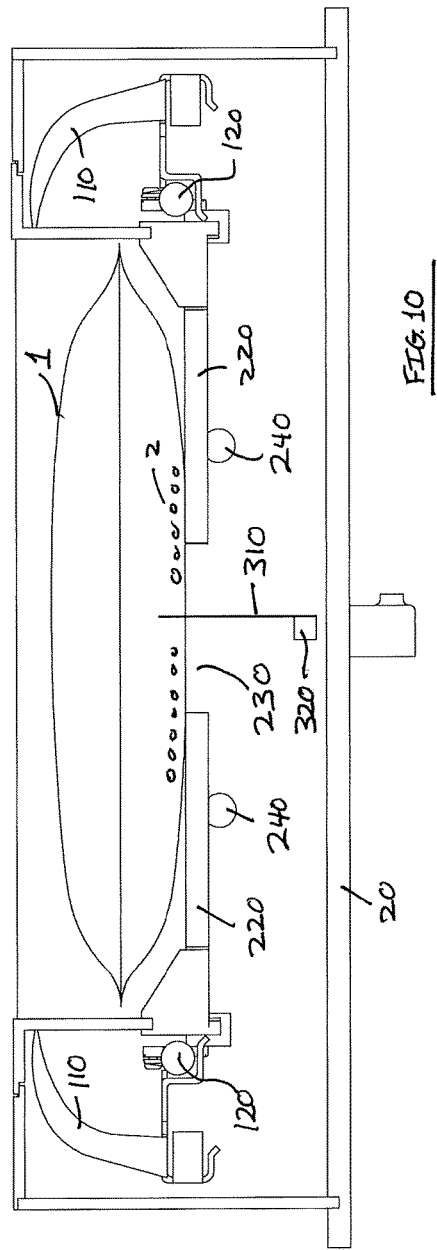

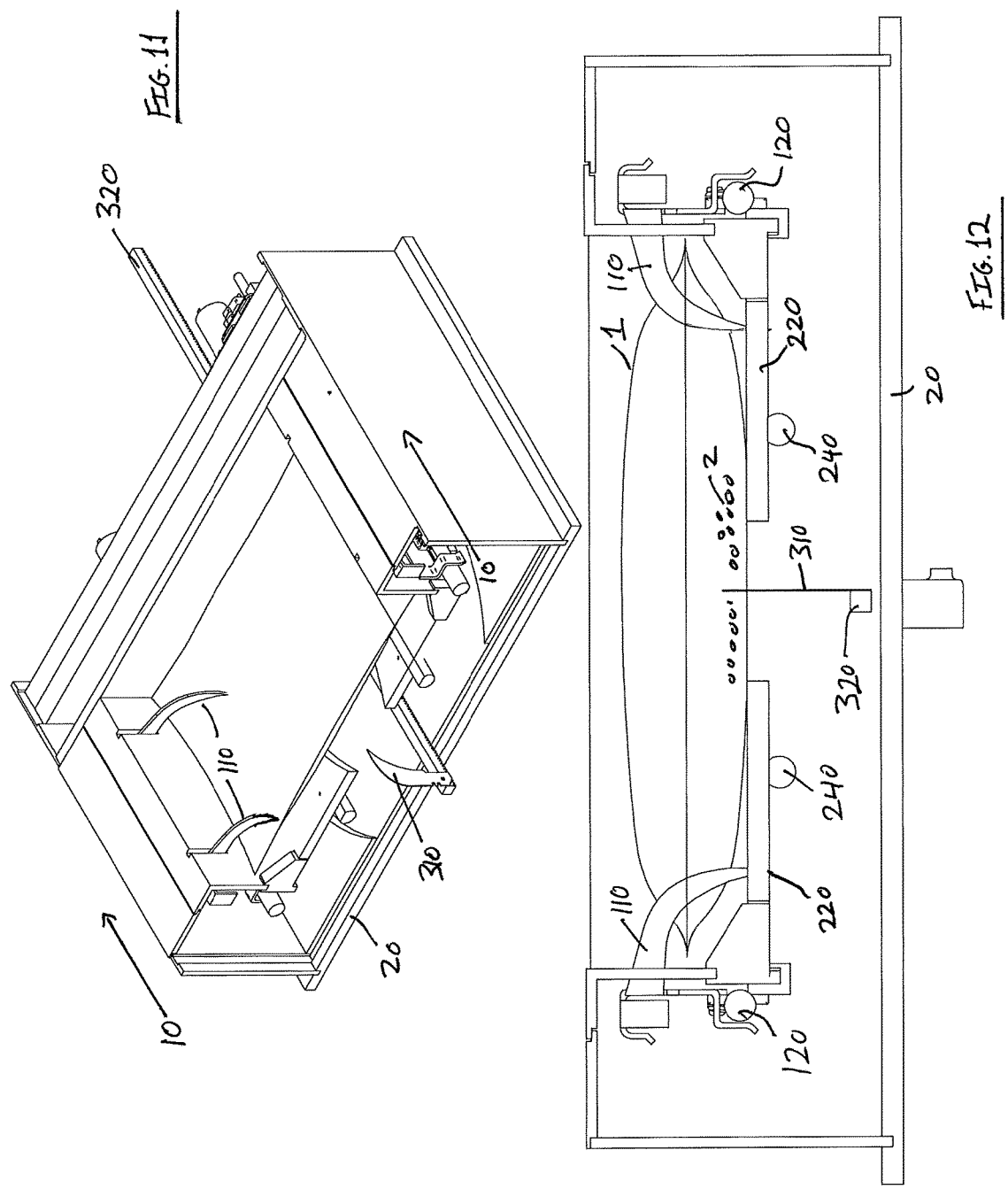

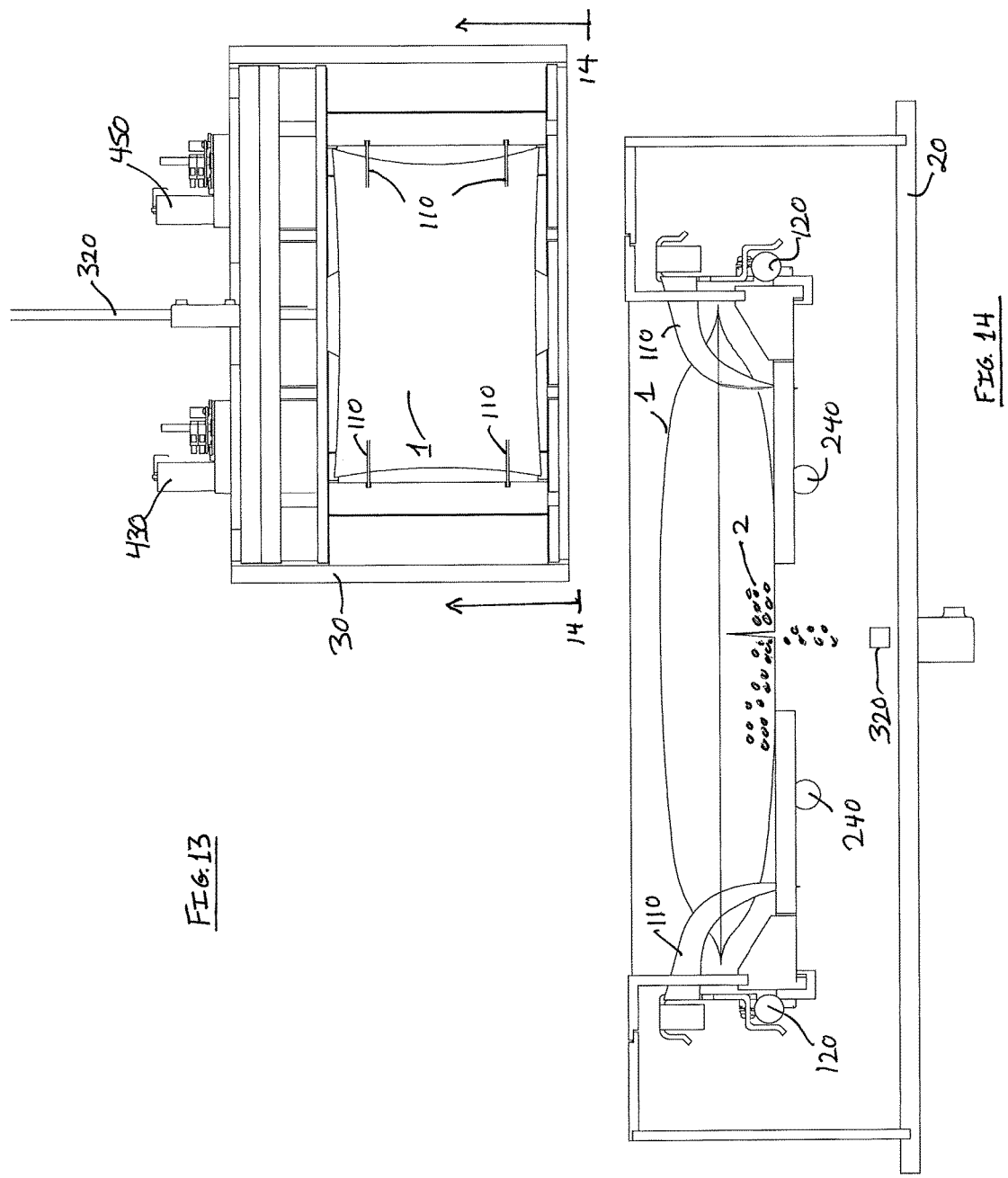

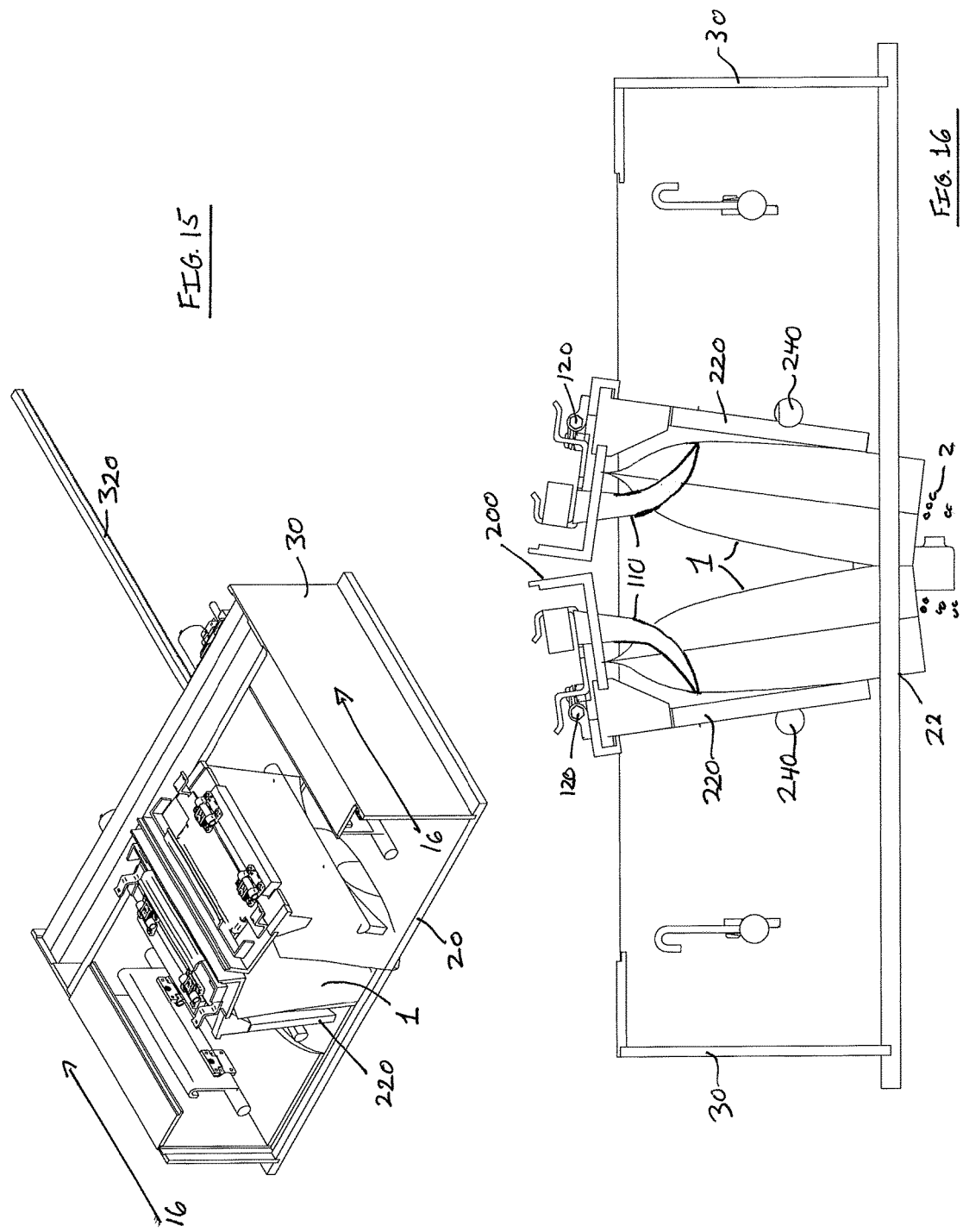

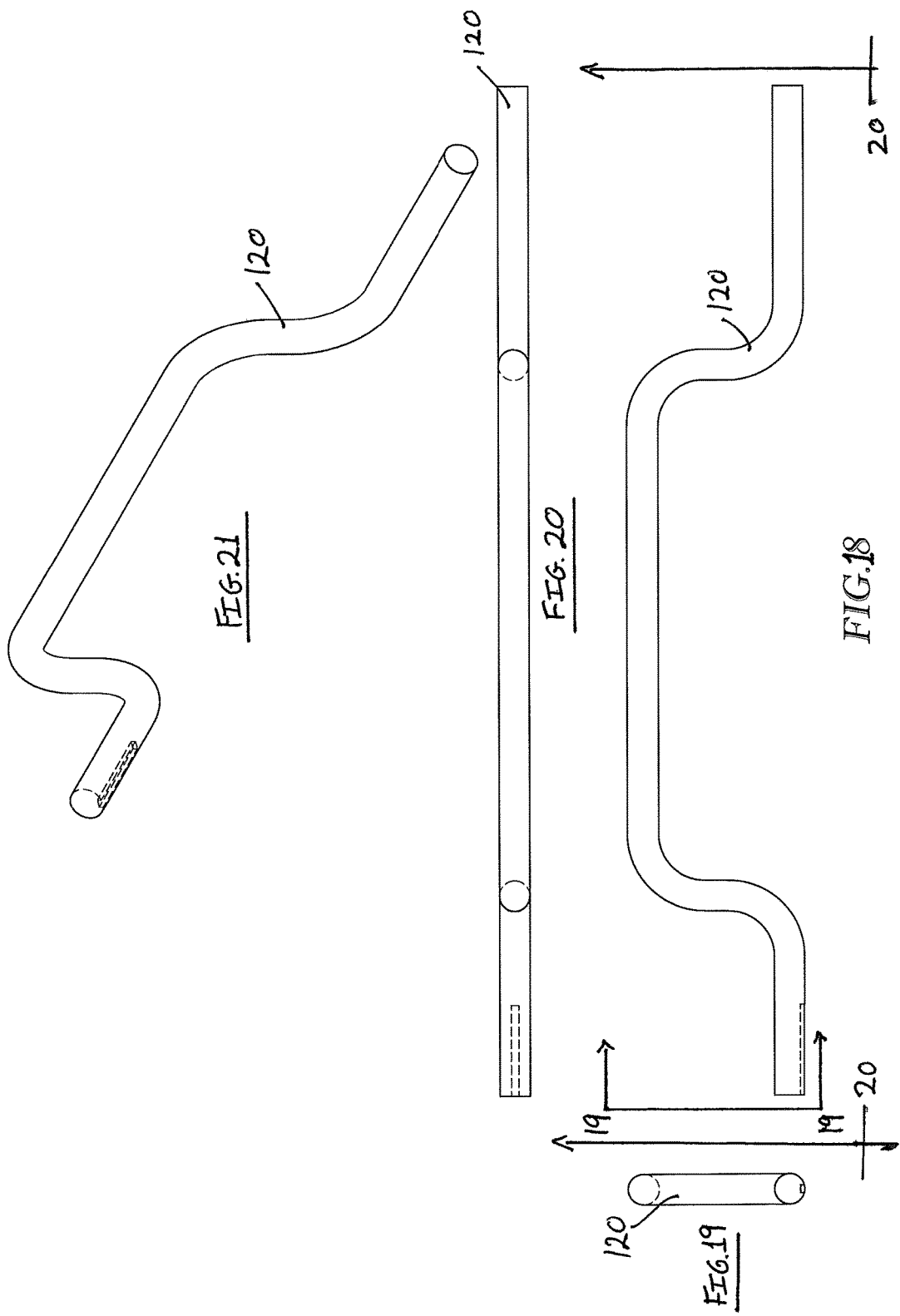

BAG OPENING SYSTEM

FIELD OF THE INVENTION

The present invention relates generally to system for mixing a solution using a liquid and a dry powder and more particularly to a system and apparatus for quickly and completely opening a dry powder bag and emptying it into a mixing receptacle to produce an acid solution for use in a hemodialysis system.

BACKGROUND OF THE INVENTION

There is a need in the medical field for mixing various acidic solutions for a wide variety of medical clinical uses. Many of these solutions are prepared on site by mixing a predetermined amount of dry acid powder with a predetermined volume of water to produce an acid solution having a desired pH. Most of these prior art acid solution mixing systems require a great deal of laborious and time-consuming handling. For example, a dry acid powder bag must be opened and a volume of powder must be measured and placed into a suitable mixing container. Then a volume of water must be carefully measured and poured into the container for mixing, either by hand or by a motorized paddle or other mixing or agitating instrument.

Once the solution is mixed a portion thereof must be tested to determine that the proper pH or solution concentration has been achieved. Where a pre-measured dry acid bag is used in the production of solution, great care must be taken to ensure complete emptying of the bag to produce a predetermined volume of solution of the desired pH. If the pH or concentration of the solution is incorrect by even a small amount, the portions must be adjusted and re-mixed, since in medical applications such as hemodialysis even a small variation in pH can have catastrophic results. In these prior art mixing systems, even where some portion of the process is automated, there is a great deal of user-intensive labor required in the mixing process.

In many dry acid powder applications, the powder can have a tendency to clump or stick to the bag sides, thereby making complete emptying of a bag difficult. Usually a bag or bags must be carefully opened by hand and emptied into a receptacle or hopper for further processing and mixing. Obviously, this procedure requires a great deal of manual labor, particularly for large batches. Each bag must be carefully opened, emptied, taking care to make sure the powder is completely removed, and then discarded by hand. In large medical systems used for hemodialysis this procedure can be quite unwieldy and unreliable, requiring repeated testing and mixing to produce consistent solution batches.

Thus there is a need in the art for a dry powder bag opening system, for example an acid solution mixing system, that minimizes user labor while assuring complete bag emptying for each bag utilized, thereby providing consistent mixing, quality control, and accurate pH in each batch of solution being prepared.

SUMMARY OF THE INVENTION

Various embodiments and aspects of the invention overcome the aforementioned deficiencies in the prior art by providing generally a system for mixing a solution and more particularly a system for automatically opening a bag of pre-measured dry acid mix powder and emptying it into a mix tank to produce a solution having a desired pH or concentration. It should be noted that while the various implementations and embodiments discussed in this specification refer mainly to a system for emptying and mixing a bag of dry acid powder to produce an acid solution, one of ordinary skill will recognize that the instant system may be utilized to open and empty a wide variety of powder bags with any of a wide variety of fluids without departing from the scope of the invention. Thus, the system described herein is not limited to the mixing of acid solutions, but rather may be implemented to mix any solution utilizing a powder or dry material contained in a bag with a liquid or fluid.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Before explaining exemplary embodiments consistent with the present disclosure in detail, it is to be understood that the disclosure is not limited in its application to the details of constructions and to the arrangements set forth in the following description or illustrated in the drawings. The disclosure is capable of embodiments in addition to those described and is capable of being practiced and carried out in various ways. Also, it is to be understood that the phraseology and terminology employed herein, as well as in the abstract, are for the purpose of description and should not be regarded as limiting.

In various aspects and embodiments the system described provides an apparatus for holding, piercing, cutting and emptying a bag of material form further processing, for example a dry powder. The combination of elements act to provide a complete emptying of powdered material from a bag, even where clumping may be present. This system and apparatus offers many advantages from existing mixing systems, which typically require hand-opening and addition of powdered materials.

In some embodiments a bag to be opened is placed on a pair of opposed rotatable doors that have an opening there between, allowing a center portion of the bag to remain unsupported above an aperture or opening to a mix tank, hopper, mix line, or other container used for further mixing and/or processing. In various aspects the doors include several slots or holes therein, through which a plurality of piercing and gripping blades may be deployed to pierce the bag being opened. The piercing blades serve multiple functions, acting to de-pressurize the bag, break up clumped material in the bag, and hold the bag securely to the rotatable doors during system operation.

In various embodiments a cutting blade is provided that is pulled along a transverse path to the bag on a bottom side thereof to open the bag directly above the door openings, thus initiating the emptying process. The cutting blade in some aspects may be actuated by a rack and pinion system that draws the blade smoothly and consistently across a bag bottom in the same location each time the system is operated.

In other aspects and embodiments of the system the pair of opposed rotatable doors can be actuated to pivot together, thus squeezing and emptying the bag being gripped by the piercing blades. In some aspects the door rotation can be cycled to assure complete bag emptying.

In other aspects and embodiments the components of the system may be operated by a controller or processor that is capable of actuating or energizing the required motors and other electro-mechanical components that may form a part of the system. In various aspects and embodiments of the invention a processor or controller is provided, having signal and/or data inputs and signal and/or data outputs for accepting and supplying various electrical signals to and from components of the invention. The controller may include a data memory for storing instructions to operate the various invention components as well as an operator interface or equivalent user input to allow an operator to receive data from the system as well as provide user commands.

In some aspects and embodiments controller may store information provided through an operator interface related to the bags of powder being emptied and mixed so that each batch that is mixed can be tracked by the powder batch number, manufacturer, sale date, and size, to mention some exemplary but non-limiting data that may be stored and tracked.

The accompanying drawings, which are incorporated and form a part of the specification illustrate exemplary but non-limiting embodiments of the disclosure, and together with the description, serve to explain the principles of the disclosure.

Those skilled in the art will appreciate that the inventive concepts and principles upon which the disclosure is based may readily be utilized as a basis for designing other structures, systems, methods, and articles of manufacture for implementing the purposes of the present disclosure. Accordingly the claims appended hereto should be construed to include such equivalent constructions without departing from the spirit and scope of the invention herein disclosed.

BRIEF DESCRIPTION OF THE FIGURES

FIG. 4 is a top view of a bag opening system in accordance with one embodiment of the invention;

FIG. 4A is view of a bag opening system taken along the line 4A-4A of FIG. 4 in accordance with one embodiment of the invention;

FIG. 5 is a partial isometric view of a bag opening system in accordance with some embodiments of the invention.

FIG. 9 is a partial isometric view of a bag opening system in accordance with one embodiment of the invention;

FIG. 10 is a view of a bag opening system taken along the line 10-10 of FIG. 9 in accordance with one embodiment of the invention;

FIG. 11 is a partial isometric view of a bag opening system in accordance with one embodiment of the invention;

FIG. 12 is a view of a bag opening system taken along the line 12-12 of FIG. 11 in accordance with one embodiment of the invention;

FIG. 13 is a top view of a bag opening system in accordance with one embodiment of the invention;

FIG. 14 is a view of a bag opening system taken along the line 14-14 of FIG. 13 in accordance with one embodiment of the invention;

FIG. 15 is a partial isometric view of a bag opening system in accordance with one embodiment of the invention;

FIG. 16 is a view of a bag opening system taken along the line 16-16 of FIG. 15 in accordance with one embodiment of the invention;

FIG. 18 is a view of a piercing blade pivot rod in accordance with one embodiment of the invention;

FIG. 19 is a view of a piercing blade pivot rod taken along the line 19-19 of FIG. 18 in accordance with one embodiment of the invention;

FIG. 20 is a view of a piercing blade pivot rod taken along the line 20-20 of FIG. 19 in accordance with one embodiment of the invention;

FIG. 21 is a view of a piercing blade pivot rod taken along the line 21-21 of FIG. 20 in accordance with one embodiment of the invention.

DETAILED DESCRIPTION OF THE PREFERRED EMBODIMENT(S)

Figure 1:
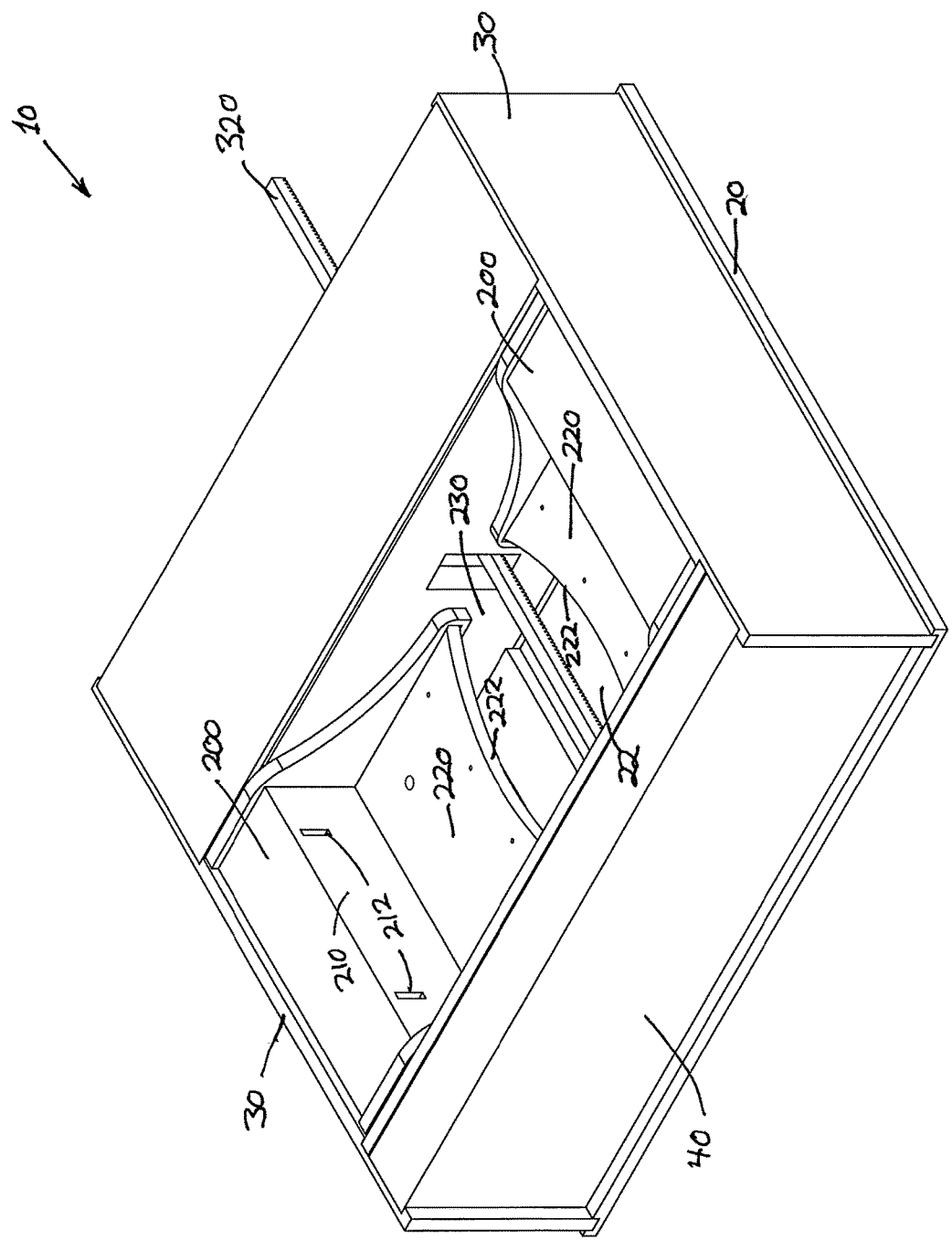
FIG. 1 is an isometric diagram of a bag opening system in accordance with one embodiment of the invention.
Figure 2:
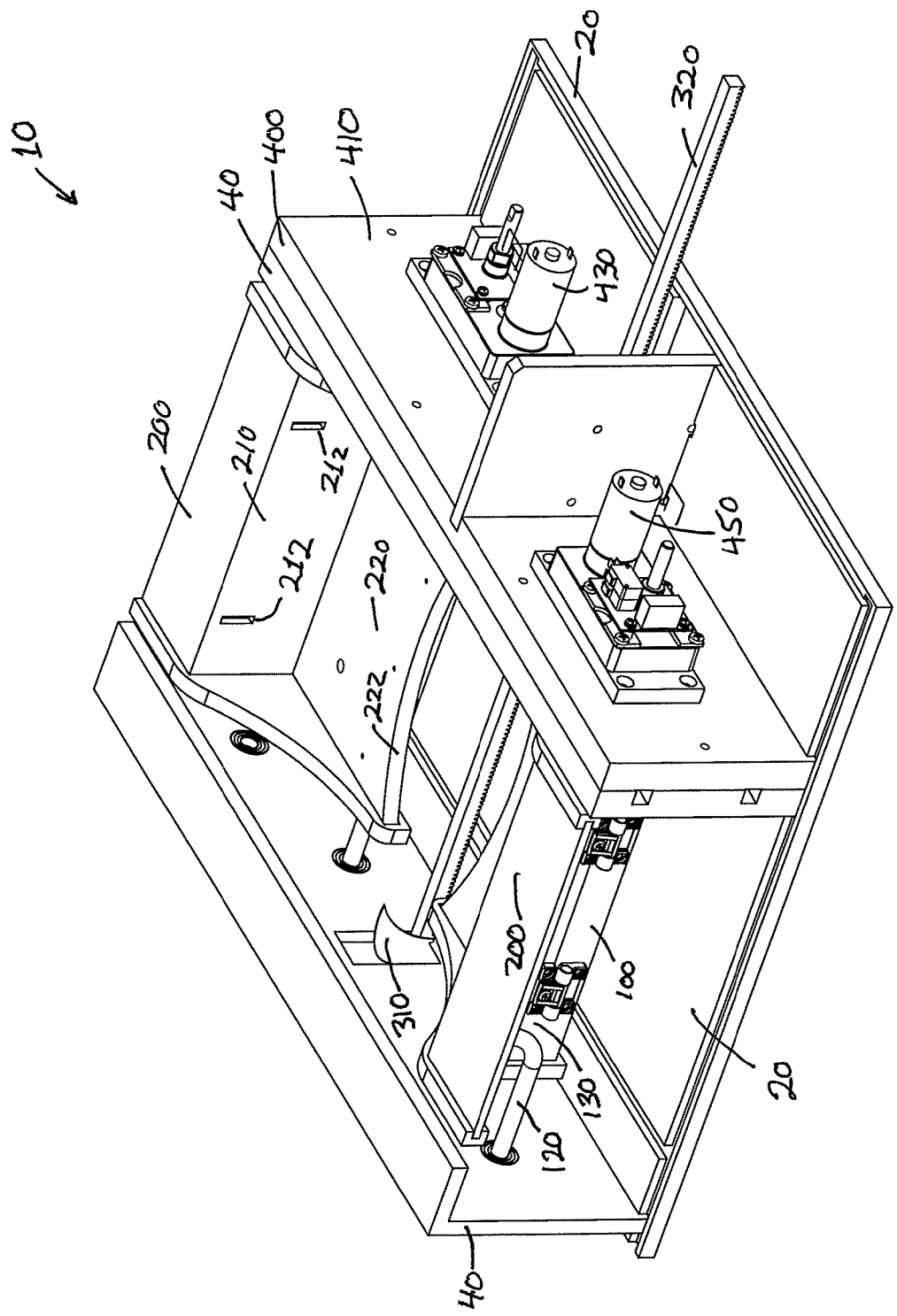
FIG. 2 is an isometric diagram of a bag opening system in accordance with one embodiment of the invention.
Figure 3:
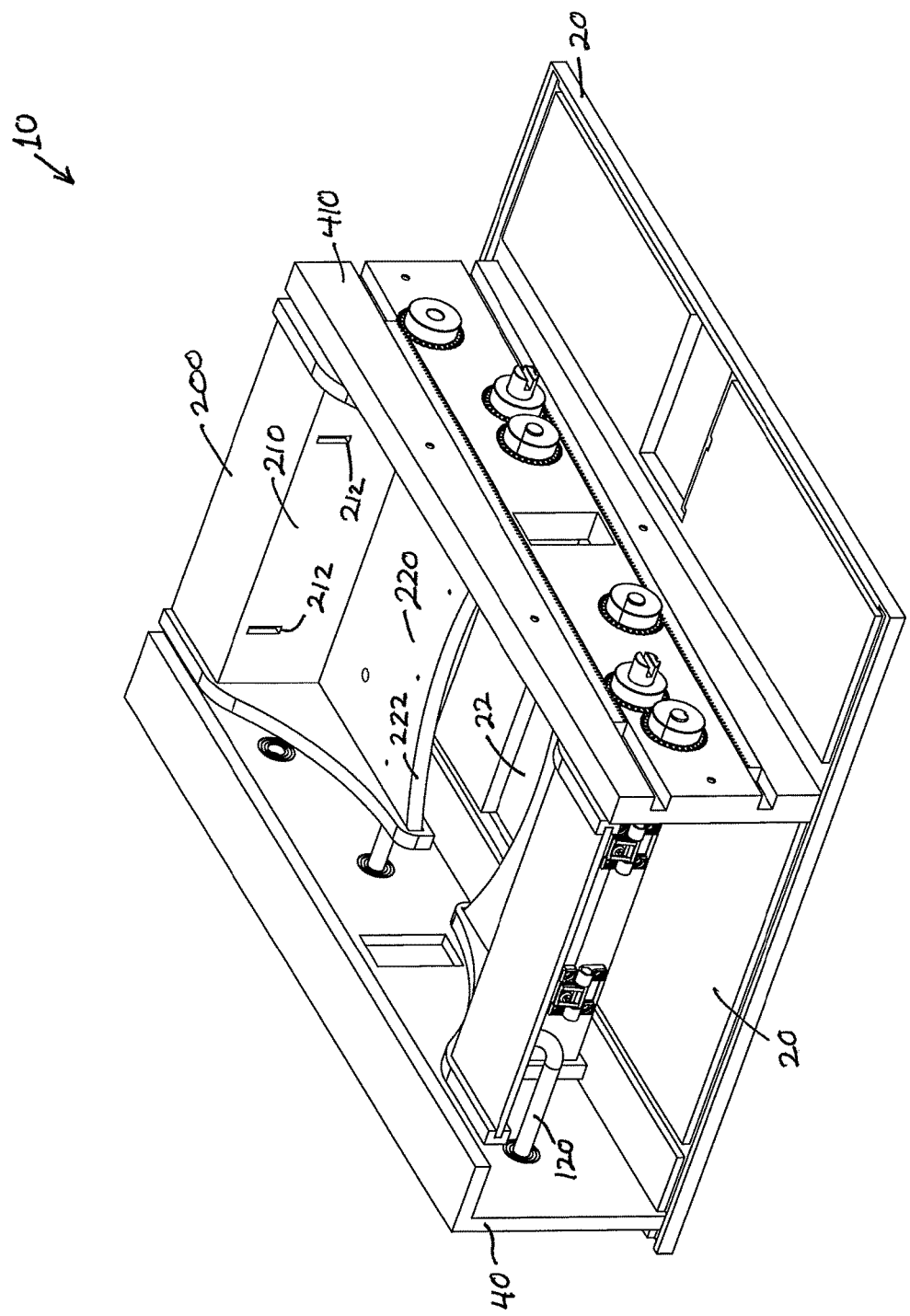
FIG. 3 is a partial isometric view of a bag opening system in accordance with one embodiment of the invention.
Figure 6:
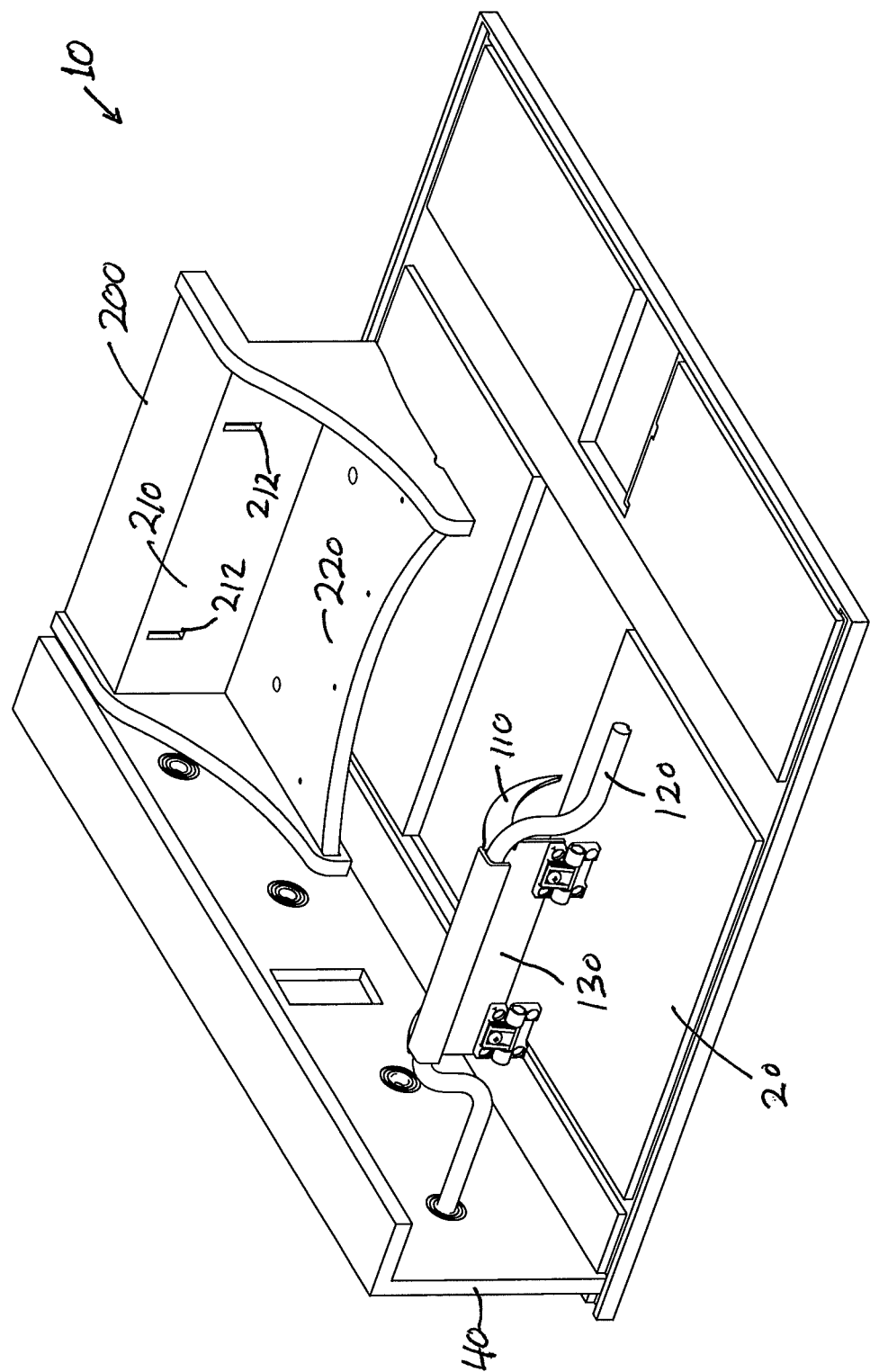
FIG. 6 is a partial isometric view of a bag opening system in accordance with one embodiment of the invention.

Referring now to the drawing Figures, and in particular FIGS. 1-3, and in accordance with a several aspects and exemplary embodiments of the present invention a bag 1 opening system 10 for opening and emptying a bag 1 containing powder 2 or any material into a hopper, mix tank, or other receptacle into which the powder 2 may be deposited for mixing or further processing includes a base 20 on which system 20 is mounted and supported. Base 20 may be generally flat in shape and may include an aperture 22 or opening in a portion thereof to permit the contents 2 of bag 1 to flow in to a hopper or other container placed below base 20 aperture 22. In some aspects and embodiments system 10 may include a pair of opposed ends 30 depending from base 20 as well as a pair of opposed sides 40 depending from base 20. Base 20, ends 30 and sides 40 generally form a box or container into which bag 1 may be placed, as will be discussed further herein below. Additionally, base 20, ends 30 and sides 40 may be formed of a material that is non-reactive with the material 1 that is disposed in the bag 1 being opened. In some aspects and embodiments base 20 may be constructed of polytetrafluoroethylene or a similar non-reactive material although a wide variety of materials may be utilized without departing from the scope of the invention.

In some aspects as shown in FIGS. 2-6 system 10 includes a bag piercing assembly 100 comprising two pairs of opposed piercing blades 110 for grasping and piercing bag 1. Each pair of piercing blades 110 is mounted to a pivot rod 120 that is capable of rotation around a central axis and that acts to move the piercing blades 110 from an open position as shown in FIG. 1 to a closed or piercing position as shown in FIG. 5, for example. In some aspects and embodiments pivot rod 120 is secured to a blade mounting block 130, to which piercing blades 110 are firmly secured. Piercing blades 110 are actuated by rotating pivot rod 120 and attached blade mounting block 130 through, for example, ninety degrees of rotation, utilizing an actuator, although it will be recognized that piercing blades 110 may be rotated more or less than 90 degrees depending upon the specific bag 1 opening application without departing from the scope of the present invention. While the various embodiments disclosed herein envision two pairs of opposed piercing blades 110 it should be understood that a larger or smaller number of piercing blades 100 may be employed in the system 10 without departing from the scope of the invention.

Referring again to FIGS. 1-5 and 14, in yet further aspects and embodiments system 10 includes a pair of opposed doors 200 that are rotatably mounted between sides 40 of system 10. Each door 200 may include a generally upright back wall 210, having at least two slots 212 therein through which piercing blades 110 may extend when they are closed. Each door 200 may additionally include a bottom portion 220 for supporting bag 1 and an inner shaped or curved edge 222 that facilitates bag 1 contents 2 dropping through aperture 22 when system 10 is operated.

In some aspects and embodiments doors 200 are rotatably secured to sides 40 at a point proximate the ends of curved edge 222 to further facilitate material exiting bag 1. In an exemplary embodiment doors 200 are secured to a door shaft 240 positioned underneath door bottom portion 220, that is rotated to force door 200 upwardly, rotating around shaft 240, thereby forcing or squeezing bag 1 to empty powder 1, as best depicted in FIGS. 15 and 16. Additionally, and referring again to FIGS. 1-5, curved edges 222 of opposed doors 200 form an aperture or void 230 over which bag 1 is unsupported so that when bag 1 is opened beneath void 230, powder 2 readily falls downwardly through aperture 22 of base 20. Similar to base 20, opposed doors 200 may be constructed of any material that is unaffected by the powder 2 being removed from bag 1. In some exemplary embodiments doors 200 may be formed of polytetrafluoroethylene.

Referring now to FIGS. 1-3 and 4-7 and in accordance with some embodiments of the invention a cutting blade assembly 300 includes a cutting blade 310 secured to a cutting gear rack 320 at an end 322 thereof. Cutting gear rack 320 is mounted to be capable of linear motion and further is disposed transversely to a longitudinal axis of base 20, and positioned between the curved edges 222 of opposed doors 220 and beneath base aperture 22. Cutting blade 310 is positioned such that it contacts the bottom of bag 1 as gear rack 320 is actuated, thereby opening bag 1 along a transverse line just above base aperture 22. In some aspects and embodiments, once bag 1 is opened by actuation of cutting blade 310, blade 310 is then returned to its original position until bag 1 is emptied, as described in detail herein below. Cutting blade 310 may be manufactured from any one of a plurality of metals or ceramics, and in some embodiments may be constructed of a material that is non-reactive with the contents 2 of bag 1.

Figure 7:
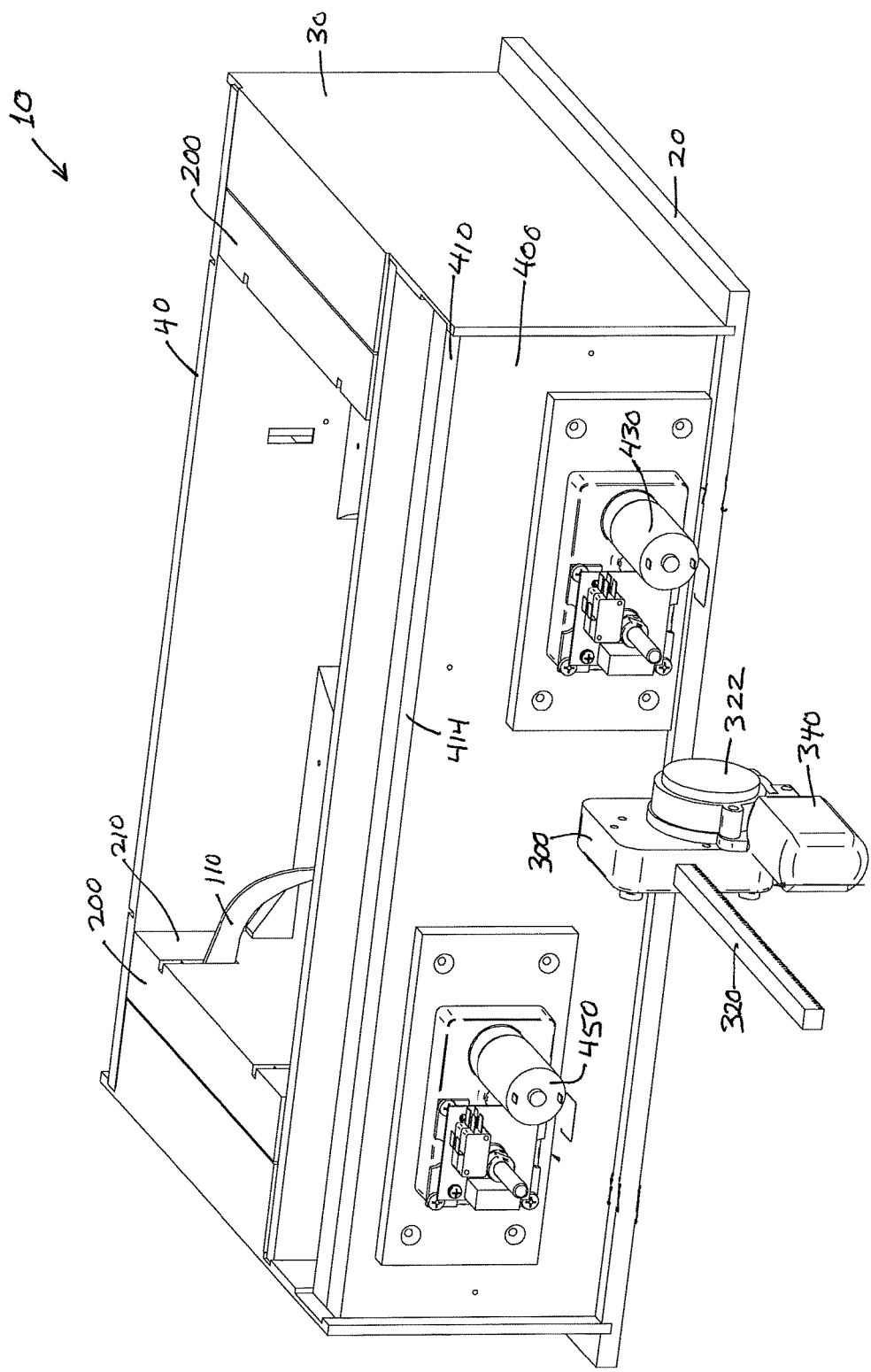
FIG. 7 is an isometric view of a bag opening system in accordance with one embodiment of the invention.
Figure 8:
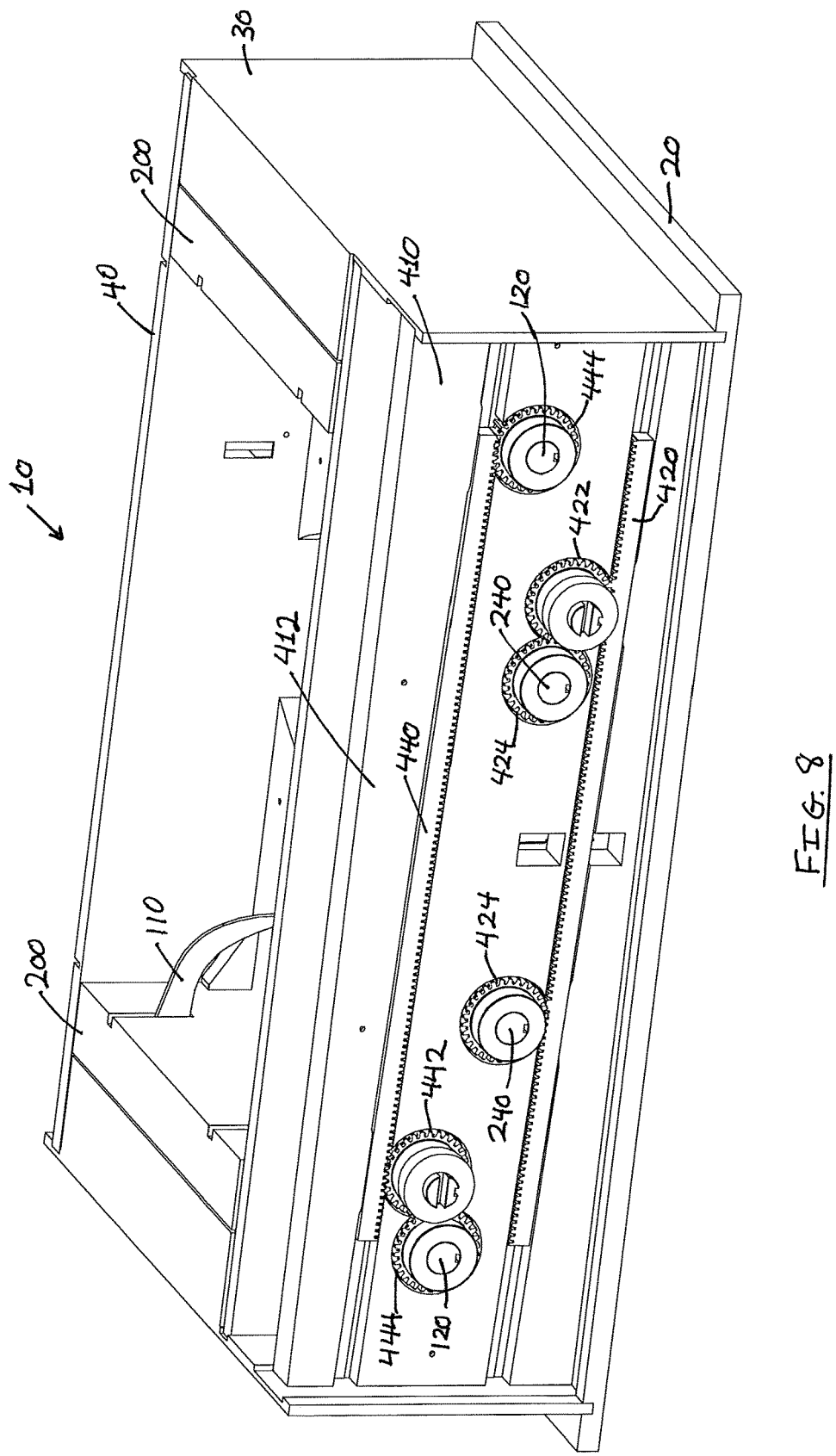
FIG. 8 is an isometric view of a bag opening system in accordance with one embodiment of the invention.
Figure 17:
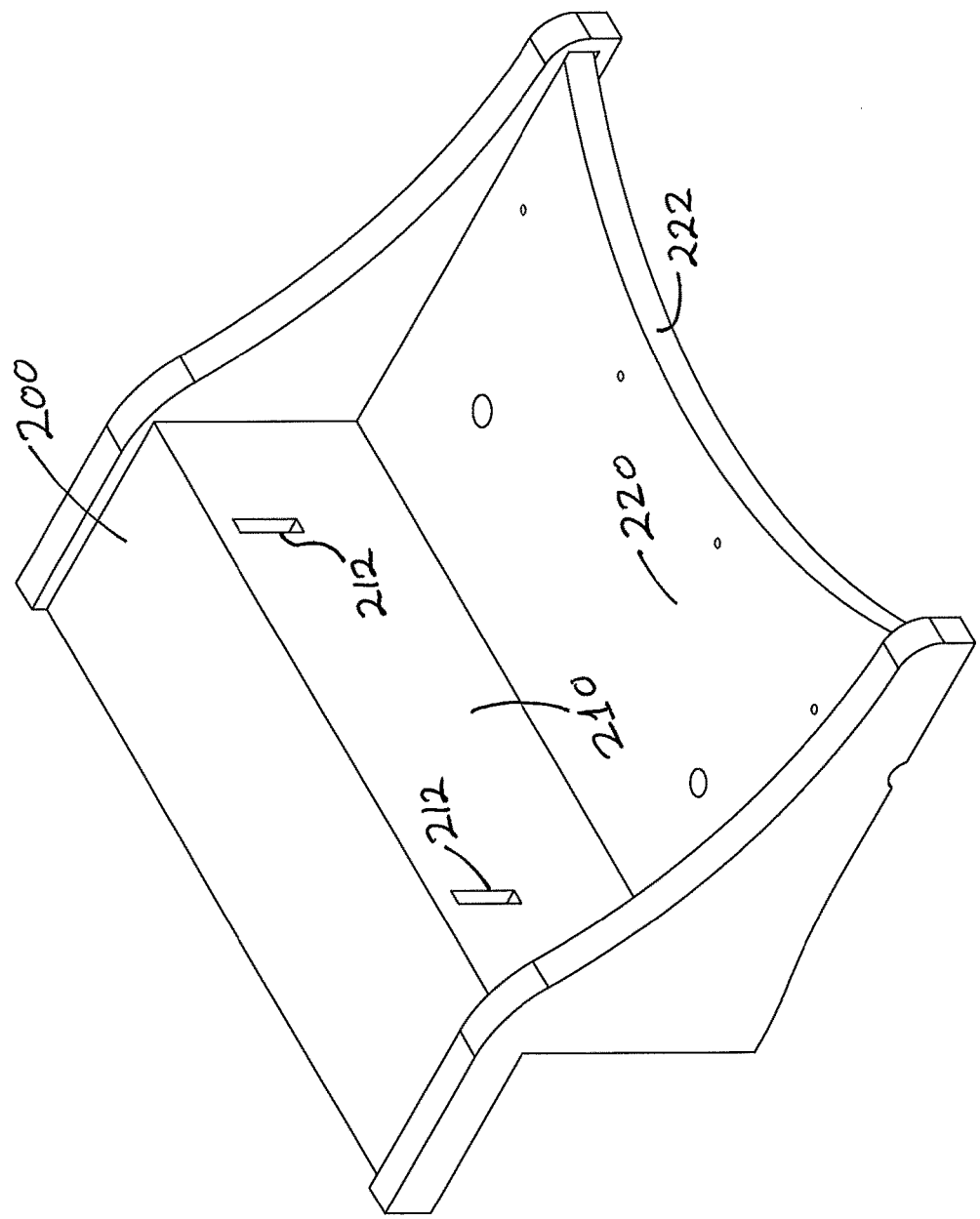
FIG. 17 is an isometric view of a door of a bag opening system in accordance with one embodiment of the invention.

Referring now to FIGS. 2, 3, 7 and 8, and in accordance with various aspects and embodiments system 10 includes an actuation assembly 400 for operating the piercing blades 110, cutting blade 310 and opposed doors 200. Actuation assembly 400 is comprised of a rack and pinion cassette 410 that is secured to one side 40 of system 10 to engage and operate pivot rods 120, door shafts 240, and cutting blade gear rack 320. Rack and pinion cassette 410 may include an inner wall 412 on which the racks and pinion gears are mounted as seen in FIG. 8, and an outer wall 414 on which a plurality of actuator motors are mounted to engage and drive the pinion gears. as best depicted in FIG. 8.

In various aspects and embodiments rack and pinion cassette 410 includes a door actuator rack 420 slidably mounted longitudinally along cassette 410 that is engaged by a door actuator pinion gear 422. Door actuator pinion gear 422 also engages one door actuator shaft gear 424, that is secured to and rotates door actuator shaft 240. The other door actuator shaft gear 424 is engaged and driven by door actuator rack 420. As shown in FIG. 7, a door actuator motor 430 is mounted to pinion gear 422 such that when actuated pinion gear 422 rotates, thereby imparting rotation to both actuator shaft gears 424, actuator shafts 240, and doors 200. In this fashion and as best seen in FIGS. 15 and 16, at a predetermined time door actuator motor 430 may be operated to force doors 200 upwardly and together thereby forcing the contents 2 of bag 1 to exit bag 1 through aperture 22.

Referring again to FIGS. 7 and 8, in a similar fashion, to the actuation of doors 200, rack and pinion cassette 410 includes a piercing blade 110 actuator rack 440 slidably mounted longitudinally along cassette 410 that is engaged by a piercing blade actuator pinion gear 442. Piercing blade actuator pinion gear 442 also engages one piercing blade pivot rod gear 444, that is secured to and rotates piercing blade pivot rod 120. The other piercing pivot rod gear 444 is engaged and driven by piercing blade actuator rack 440. As shown in FIG. 7, a piercing blade actuator motor 450 is mounted to pinion gear 442 such that when actuated pinion gear 442 rotates, thereby imparting rotation to both pivot rod gears 444, pivot rods 120, and piercing blades 110. In this fashion and as best seen in FIGS. 9-12, at a predetermined time piercing blade actuator motor 450 is operated to force doors piercing blades 110 to rotate and thereby puncture and grip bag 1, holding it securely while system 10 operates to cut open and empty bag 1, as will be described in detail herein below.

Referring to FIGS. 7 and 9-14 and in accordance with various aspects and embodiments cutting gear rack 320 is actuated by a cutting pinion gear 322 that is mounted proximate an end of gear rack 320 on outer wall 414 of rack and pinion cassette 410. A cutting blade motor 340 is also mounted to engage and drive cutting pinion gear 322, thereby moving cutting gear rack 320 transversely across base 20, and engaging and cutting bag 1 with cutting blade 310. Thus when cutting blade motor 340 is actuated, cutting blade 310 operates to open bag 1, thereby initiating the emptying of bag 1.

It should be noted that in various aspects cutting blade motor 340, door actuator motor 430, and piercing blade actuator motor 450 may be electrically operated servomotors, or similar AC or DC electrical motors as may be required for a given bag 1 opening system. A wide variety of motors can be used as cutting blade motor 340, door actuator motor 430 and piercing blade actuator motor without departing from the scope of the present invention.

Figure 22:
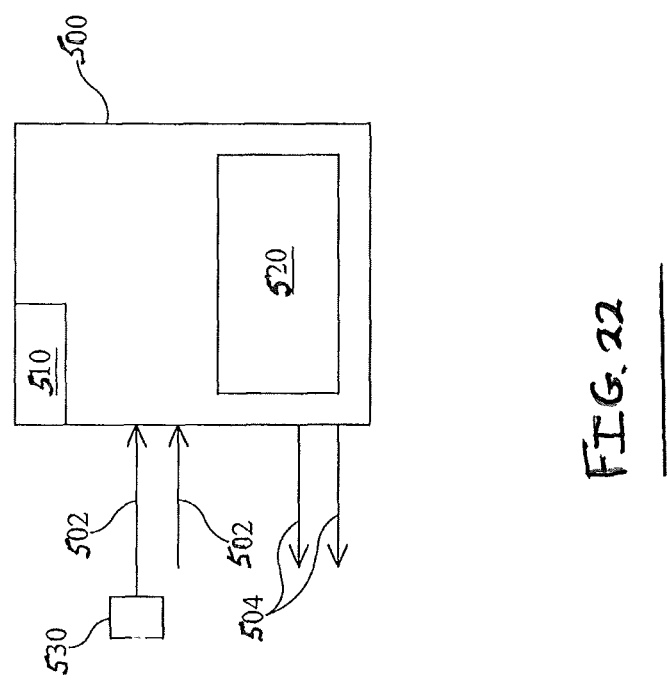
FIG. 22 is a block diagram of a controller in accordance with one embodiment of the invention.

In various aspects and embodiments of the invention as depicted in FIG. 22 a processor 500 or controller may be provided, having signal and/or data inputs 502 and signal and/or data and/or power outputs 504 for accepting and supplying various electrical signals to and from components of the invention such as servo-motors, limit switches, resolvers and the like. Controller 500 may include a data memory 510 for storing instructions to operate the various invention components as well as an operator interface 520 or equivalent user input to allow an operator to receive and view data and various system 10 operating parameters as well as provide user commands thereto. Processor 500 inputs 502 and outputs 504 are in some embodiments operatively coupled to the actuator motors utilized to actuate piercing blades 110, doors 200, and cutting blade 310 of system 10. Processor 500 may further be operatively coupled to a bar code scanner 530 or similar device for detecting, scanning and storing bag 1 and fluid batch information in data memory 510. Furthermore, operator interface 120 may be used to initiate operation of system 10 by selecting a "start" or "open bag" icon to begin an operation sequence.

Referring now to FIGS. 9-14 system 10 performs a bag 1 opening and emptying operation once a user places a bag 1 of powder 2 or other similar material centered over doors 200. Controller 500 may be in some embodiments provided with a suitable program or instruction set that enables controller 500 to operate or energize system 10 components according to the following exemplary but non-limiting embodiments. Initially, operator interface 520 may be utilized to select a "start" icon or pushbutton to initiate bag 1 opening. Controller 500 then energizes the requisite outputs 504 to actuate motors in the following sequence. Initially, piercing blade 110 actuator motor 450 is energized to rotate piercing blades 110 to rupture and grip bag 1 as seen in FIGS. 11-12. Once bag 1 has been firmly grasped, the cutting blade 310 motor 340 is actuated thereby forcing cutting blade 310 across the bottom of bag 1 and cutting it open. Powder 2 from bag 1 begins dropping through doors 200 and aperture 22 into a receptacle, mix tank, mix line or other container (not shown). Controller 400 then energizes door actuator motor 430, forcing doors 200 to rotate around shafts 240 and open, thereby opening bag 1 to permit powder 2 to empty through aperture 22. After a predetermined timer period, door actuator motor 430 is reversed, returning doors to their closed position. In some aspects and embodiments door actuator motor is cycled to open and close doors 200 a predetermined number of times, and/or through a predetermined arc of rotation to facilitate complete emptying of bag 1. Furthermore, cutting blade motor 340 return blade 310 to its initial position and piercing blade motor 450 returns piercing blades 110 to their initial position. The empty bag 1 can then be removed from system 10.

The term "processor" or alternatively "controller" is used herein generally to describe various apparatus relating to the operation of one or more light sources. A controller can be implemented in numerous ways (e.g., such as with dedicated hardware) to perform various functions discussed herein. A "processor" is one example of a controller which employs one or more microprocessors that may be programmed using software (e.g., microcode or machine instructions) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein.

Various storage media may be fixed within a processor or controller or may be transportable, such that the one or more programs stored thereon can be loaded into a processor or controller so as to implement various aspects of the present disclosure discussed herein. The terms "program" or "computer program" are used herein in a generic sense to refer to any type of computer code (e.g., software or microcode) that can be employed to program one or more processors or controllers.

The term "user interface" as used herein refers to an interface between a user or operator and one or more devices that enables interaction between the user and the device(s). Examples of user interfaces that may be employed in various implementations of the present disclosure include, but are not limited to, switches, potentiometers, buttons, dials, sliders, a mouse, keyboards, keypads, various types of game controllers (e.g., joysticks), track balls, display screens, various types of graphical user interfaces (GUIs), smartphones, watches, tablets, personal computing platforms, touch screens, microphones and other types of sensors that may receive some form of human-generated stimulus and generate a signal in response thereto.

The terms "motor" or "actuator motor" used herein may refer to any device used to operate the pinion gears or other actuation mechanisms that form a part of system 10. The motors referred to in the various embodiments can be actuated electrically, and may include analog or digital position feedback outputs operatively coupled to controller inputs that are indicative of motor position. Additionally, motors may be servo-motors, DC motors, or AC motors without departing from the scope of the invention.

The foregoing detailed description of the embodiments of the invention is presented primarily for clearness of understanding and no unnecessary limitations are to be understood or implied therefrom. Modifications to the present invention in its various embodiments will become obvious to those skilled in the art upon reading this disclosure and may be made without departing from scope of the invention and the claims appended hereto.

We claim:

1. A system for opening and emptying a bag of material comprising:
    a base having a pair of opposed sides depending there from and a central aperture therein;
    a pair of opposed doors rotatably mounted on a pair of door shafts between said sides, each door having a bottom portion terminating in an edge, the edges of the pair of opposed doors forming an opening;
    a plurality of piercing blades pivotally mounted to said base on a pivot rod, said blades capable of pivoting to pierce said bag; and
    a cutting blade mounted transversely below the opening of said opposed doors, said cutting blade capable of linear motion across the opening.

2. The system as claimed in claim 1 comprising:
    a generally upright back wall depending from each of said doors, whereby said bag is positioned between said opposed back walls and over said opening.

3. The system as claimed in claim 2 comprising:
    a plurality of slots through said opposed doors, whereby said piercing blades pivot through said slots.

4. The system as claimed in claim 3 comprising:
    an actuation assembly for rotating said doors, pivoting said piercing blades and moving said cutting blade.

5. The system as claimed in claim 4 wherein said actuation assembly comprises:

a rack and pinion cassette secured to one of said sides of said base, said cassette comprising:
  a door actuator rack gear and a door actuator pinion gear, said door actuator rack gear engaging said door shafts;
  a piercing blade actuator rack gear and a piercing blade pinion gear, said piercing blade actuator rack gear engaging said piercing blade pivot rods; and
  a cutting gear rack to which said cutting blade is secured, said gear rack mounted transversely below the opening of said opposed doors, and a cutting pinion gear for engaging said cutting blade gear rack.

6. The system as claimed in claim 5 comprising;
a door actuator motor driving said door actuator pinion gear to open and close said doors;
a piercing blade actuator motor driving said piercing blade pinion gear to open and close said piercing blades; and
a cutting blade motor driving said cutting pinion gear to operate said cutting blade.

7. The system as claimed in claim 6 comprising;
a controller having a data memory and a plurality of inputs and outputs for supplying and receiving signals, and an operator interface operatively coupled to said controller for receiving user commands, said controller outputs operatively coupled to said door actuator motor, said piercing blade actuator motor, and said cutting blade motor.

8. An apparatus for opening and emptying a bag of material comprising:
a base having a pair of opposed sides and a central aperture therein through which material may empty;
a pair of opposed doors each mounted on a rotatable door shaft between said sides, each door having a bottom portion terminating in an edge, the edges of the pair of opposed doors forming an opening and each door having a back, said bag being positioned between said door backs and resting on said bottom portions;
two pairs of opposed piercing blades pivotally mounted on a pivot rod, said blades capable of pivoting to pierce said bag; and
a cutting blade mounted on a rack positioned transversely below the opening of said opposed doors, said cutting blade capable of linear motion across the opening.

9. The apparatus as claimed in claim 8 comprising:
a pair of slots in each door back whereby said piercing blades pivot through said slots to grip a bag positioned on said door.

10. The apparatus as claimed in claim 9 comprising:
a rack and pinion cassette secured to one of said sides of said base, said cassette comprising:
  a slidable door actuator rack and a door actuator pinion gear, said door actuator rack engaging said door shafts to effect rotation thereof and rotate said doors between a closed and an open position;
  a slidable piercing blade actuator rack and a piercing blade pinion gear, said piercing blade actuator rack gear engaging said piercing blade pivot rods to effect rotation thereof and rotate said piercing blades between a closed and an open position; and
  a slidable cutting blade rack to which said cutting blade is secured, said cutting blade rack mounted transversely below the opening of said opposed doors, and a cutting pinion gear for engaging said cutting blade rack.

11. The apparatus as claimed in claim 10 comprising;
a door actuator motor driving said door actuator pinion gear to open and close said doors;
a piercing blade actuator motor driving said piercing blade pinion gear to open and close said piercing blades; and
a cutting blade motor driving said cutting pinion gear to operate said cutting blade.

12. The apparatus as claimed in claim 11 wherein said door actuator motor, said piercing blade actuator motor and said cutting blade motor are servomotors.

13. The apparatus as claimed in claim 11 comprising;
a controller having a data memory and a plurality of inputs and outputs for supplying and receiving signals, and an operator interface operatively coupled to said controller for receiving user commands, said controller outputs operatively coupled to said door actuator motor, said piercing blade actuator motor, and said cutting blade motor.

14. The apparatus as claimed in claim 13 whereby said controller executes a set of instructions to:
operate said piercing blade actuator motor to pierce said bag;
operate said cutting blade actuator motor to cut said bag;
operate said door actuator motor to fold and empty said bag through said base aperture.

15. The apparatus as claimed in claim 14 whereby said controller executes a set of instructions to:
operate said door actuator motor to fold and empty said bag a predetermined number of times to empty said bag.

16. The apparatus as claimed in claim 14 whereby said controller executes a set of instructions to:
operate said door actuator motor to fold and empty said bag a predetermined number of times through a predetermined range of motion to empty said bag.

17. The apparatus of claim 8 wherein said doors and said base are formed of polytetrafluoroethylene.

* * * * *